United States Patent [19]

Garrison et al.

[11] Patent Number: 5,697,390
[45] Date of Patent: Dec. 16, 1997

[54] PROCESS FOR PRODUCING FILLED POLYTETRAFLUOROETHYLENE RESIN COMPOSITE MATERIALS AND PRODUCTS

[75] Inventors: David S. Garrison, Yardley; David A. Delgado, Levittown, both of Pa.; Patricia J. Deeney, Lawrenceville, N.J.; David E. Newman, Huntington Station, N.Y.

[73] Assignee: Coltec Industries Inc, Charlotte, N.C.

[21] Appl. No.: 608,304

[22] Filed: Feb. 28, 1996

Related U.S. Application Data

[63] Continuation-in-part of Ser. No. 385,724, Feb. 8, 1995, Pat. No. 5,501,827, which is a continuation of Ser. No. 107,050, Aug. 17, 1993, abandoned, which is a continuation-in-part of Ser. No. 10,979, Jan. 29, 1993.

[51] Int. Cl.⁶ .......................... A61C 15/04; B28B 11/16; D01F 6/12
[52] U.S. Cl. .......................... 132/321; 264/122; 264/127; 264/146; 264/211; 264/464; 264/482
[58] Field of Search .......................... 132/321; 264/122, 264/127, 146, 211, 464, 482; 524/80

[56] References Cited

U.S. PATENT DOCUMENTS

| | | | |
|---|---|---|---|
| 3,793,287 | 2/1974 | Fritz et al. | 524/419 |
| 4,385,093 | 5/1983 | Hubis | 264/288.4 |
| 4,440,879 | 4/1984 | Kawachi et al. | 524/434 |
| 4,859,332 | 8/1989 | Dillon | 264/127 |
| 4,963,609 | 10/1990 | Anderson et al. | 524/413 |
| 5,033,488 | 7/1991 | Curtis et al. | 132/321 |
| 5,209,251 | 5/1993 | Curtis et al. | 132/321 |
| 5,220,932 | 6/1993 | Blass | 132/321 |
| 5,288,552 | 2/1994 | Hollenbaugh, Jr. et al. | 264/127 |
| 5,503,842 | 4/1996 | Fazon et al. | 132/321 |
| 5,518,012 | 5/1996 | Dolan et al. | 132/321 |

FOREIGN PATENT DOCUMENTS

| | | |
|---|---|---|
| 0256422 | 7/1991 | European Pat. Off. . |
| 2215116 | 7/1992 | United Kingdom . |

OTHER PUBLICATIONS

Ross, J.A., DuPont publication PIB #34—Fine Powder Blending Machines, Principles, Performance (Oct. 1968) Garlock Plastomer Products, Trost Air Impact Pulverizers (Undated).

*Primary Examiner*—Peter A. Szekely
*Attorney, Agent, or Firm*—Cummings & Lockwood

[57] ABSTRACT

A process is provided for producing an additive-containing PTFE or other fluorocarbon polymer resin which achieves substantially complete and thorough homogeneous distribution of the selected additive within the polymer matrix. The selected additive and polymer are blended and then subjected to an air milling in an air impact pulverizer to achieve particle to particle impact and the homogeneous distribution of the additive in and among the polymer particles. The milled polymer-additive composite is paste extruded and further processed to form additive-containing PTFE products such as dental floss, insulating or conductive materials, laser markable materials, abrasion resistance materials and the like.

33 Claims, 3 Drawing Sheets

PROCESS FOR PRODUCING FILLED POLYTETRAFLUOROETHYLENE RESIN COMPOSITE MATERIALS AND PRODUCTS

This application is a continuation-in-part of U.S. patent application Ser. No. 08/385,724, filed Feb. 8, 1995, now U.S. Pat. No. 5,501,827 which is a continuation of Ser. No. 08/107,050 filed Aug. 17, 1993 now abandoned, which is a CIP of Ser. No. 08/010,979 filed Jan. 29, 1993 now abandoned.

TECHNICAL FIELD

The present invention relates generally to processes for producing polytetrafluoroethylene and other fluorocarbon polymer resin products and particularly to a process for producing a filled or additive-containing polytetrafluoroethylene composite material and to products produced thereby.

BACKGROUND OF THE INVENTION

Fluorocarbon polymer resins and polytetrafluoroethylene resins, in particular, in their various forms have found use in myriad applications in the years since this versatile material was first discovered. Products made from polytetrafluoroethylene (PTFE) resins have taken many forms, ranging from fibers to sheets. Processes for forming such products are well known. However, it has often been desirable to incorporate different materials into the polytetrafluoroethylene and other fluorocarbon polymer resins to give the end products selected characteristics. For example, the color of the fluorocarbon polymer resin may be desired to be changed by the addition of colorant or pigment. Processing chemicals, such as lubricants and the like, may be incorporated into fluorocarbon polymer resins to facilitate the formation of certain types of products.

Much emphasis has been placed in recent years on the processing of PTFE resins in fine powder form to produce various products. Typically, as is discussed in DuPont publication PIB #34 entitled "Fine Powder Blending Machines, Principles, Performance" from E. I. DuPont de Nemours & Co., Inc., these PTFE resins are processed by paste extrusion techniques to form tubing, tape, film, wire insulation and similar products. In this process a preform of a selected PTFE resin is forced through a reducing cone transition section in the extrusion equipment to a die land, which elongates the resin to produce axial fiber formation or fibrillation of the polymer as it travels through the cone and the die. The quality of the final product is dependent, in large part, on the degree and orderliness of the fibrillation. A lubricant, usually a hydrocarbon, is blended with the PTFE resin to modulate this morphological rearrangement through hydraulic and frictional influence. The blend level and distribution of lubricants, pigments and fillers in the PTFE resin may significantly affect the success of the extrusion and of the final product thus produced. The objective to be achieved during blending is the distribution of these additives in, among, and on the fine powder particles of the PTFE or other fluorocarbon polymer resin. However, the achievement of an optimum blend level or distribution has, in actuality, been quite difficult. A primary obstacle to achieving substantially complete and thorough distribution of additive particles within a fine powder PTFE resin has been the recognition by the industry that damage to the PTFE in the form of shear and large agglomerate formation occurs when fine powder resins are subjected to high energy blending systems. Products formed from damaged PTFE resins and which include areas of shear or large agglomerates will be flawed. For example, color will not appear uniform, and the conductivity of electrically conductive materials will be adversely affected.

Many different useful products based on a filled or pigmented paste extruded PTFE resin have been proposed. Insulated conductors, for example, have been formed from pigmented PTFE. In many instances it is desirable to mark insulated conductors to provide information to persons installing or using them. Such marking can often be done easily by color coding or by simple printing. As long as the material will accept ink, the only real limit on the amount of information which can be included is the available surface area. However, in the case of insulated conductors produced from PTFE, such marking has been difficult due primarily to the chemical and physical attributes of the fluoropolymer. In some instances, colored pigments or dyes have been used, but the amount of information that can be encoded is limited. Furthermore, color coding may be of little or no use to those persons who are fully or partially colorblind.

Efforts have been made to incorporate into PTFE resins photosensitive fillers which react to subsequent laser radiation to produce the desired markings. One such recently developed marking method is described in detail in U.K. Patent No. 2,215,116. An earlier effort to provide satisfactory laser marking of such resins is described in European Patent Application No. 256,422. While each of these publications describes materials and processes which have some utility, each also has shortcomings. European Patent Application No. 256,422 discloses a two-layered insulation in which a portion of the outer layer is laser etched to permit a portion of the inner layer of differing color to become visible. Obviously, making a two-layered material is more difficult, time consuming and costly, and, when the marking is done, portions of the outer layer have been physically degraded and are thus less useful as electrical insulating material. U.K. Patent No. 2,215,116 describes the laser marking of a single layer insulation material having a photosensitive filler with minimal material degradation. However, fillers with very small particle sizes are used in these prior art materials, and the results in practice have not been completely satisfactory, primarily because of the insufficient stability of the color contrast after heat aging.

U.S. Pat. Nos. 3,793,287 to Fitz et al.; 4,440,879 to Kawachi et al.; and 4,963,879 to Anderson et al. all describe methods for making filled polyfluorotetraethylene. However, this art acknowledges the difficulties encountered both with processing and in the final product when the structure of the resin is damaged by, for example, grinding in a ball mill. None of the methods disclosed in this art suggests that substantially complete distribution of fillers, pigments or other additives within a PTFE or other fluoropolymer resin can be achieved by their application. Moreover, it is suggested that some known methods of blending PTFE resins with additives damage the resin so that the resulting blend cannot be processed to produce an acceptable product. The use of an aqueous dispersion of PTFE and the selected additive forms the basis for the processes described in these patents.

Other products based on filled or additive-containing PTFE and similar resins have also been proposed. U.S. Pat. No. 5,288,552 to Hollenbaugh, Jr. et al., for example, discloses an expanded microporous PTFE sheet which may be filled with particulate fillers and processed to produce continuous PTFE fibers with substantially round profiles. U.S. Pat. No. 4,385,093 to Hubis discloses a multi-component, porous PTFE article that may optionally contain up to 50% by weight of a filler. Incorporation of the filler is accomplished by co-coagulation with the PTFE in a non-stabilized dispersion, which does not insure a complete and thorough distribution of the filler particles in, on and around the PTFE particles. In co-coagulation, PTFE particles of around 0.2 microns are coagulated in the midst of an additive while in suspension. This does give enhanced dispersion; however, mechanical properties and heat aging are inferior in the final product, and this is a lengthy and expensive method.

However, to date, the potential applications of PTFE have been limited because of blending difficulties. The manufacture of composite materials from PTFE has been limited by the absence of a liquid phase, necessitating the blending of PTFE in the solid phase with any desired additives, which may be in particulate, liquid or fiber form. Raw fine powder PTFE is typically supplied in particulate form, and the known blending methods produce a PTFE-additive blend in which additives are limited to the outer surface of the PTFE particles. The resulting product is a discontinuous compound with varying distribution of additive on a macroscopic scale because the additive cannot penetrate the solid PTFE particles.

The prior art has failed to provide a method for producing an additive-filled PTFE or fluorocarbon polymer resin material which achieves a complete and thorough macroscopic and microscopic homogeneous distribution of the additive in, on and around the resin.

SUMMARY OF THE INVENTION

It is a primary object of the present invention, therefore, to overcome the disadvantages of the prior art and to provide a method for producing an additive-filled PTFE or fluorocarbon polymer resin material which achieves a complete and thorough macroscopic and microscopic distribution of the additive in, on and around the PTFE.

It is another object of the present invention to provide a method for completely and thoroughly distributing additives in particulate, liquid or fiber form homogeneously with PTFE resin particles which retains the integrity of the PTFE resin.

It is a further object of the present invention to provide a method for producing additive-filled PTFE resin products characterized by substantially complete homogeneous distribution of the additive in, on and around the PTFE resin particles.

It is yet another object of the present invention to produce PTFE based electrical insulation materials which can be marked by exposure to laser radiation and which will retain a high degree of color contrast after heat aging.

It is yet a further object to provide PTFE resin based electrical insulation materials which can be marked by exposure to laser radiation without damage to the PTFE resin material.

It still another object of the present invention to provide a method for making PTFE resin based electrical insulation materials which produces a homogeneous composition of material so that subsequent laser marking will be of substantially uniform contrast throughout the extent of the material.

It is a still further object of the present invention to provide a method for making a fluoride-filled PTFE resin based filament suitable for use as a dental floss.

The foregoing objects are accomplished by providing a method for making an additive-filled PTFE or fluorocarbon polymer resin based material which produces a microscopically and macroscopically homogeneous distribution of the selected additive in, on and around the resin particles within the resin matrix. The method of the present invention employs a selected PTFE or other fluorocarbon polymer resin in powder form. Depending upon the initial particle size of the additive or filler selected for incorporation into the PTFE or other resin, an optional preliminary air milling step may be required to produce an optimum additive or filler particle size. The selected resin is dry blended with a selected additive or filler under selected conditions to produce a resin-additive blend. The resin-additive blend is introduced as the feed stream to a jet mill where it is subjected to the particle to particle impact produced by an air milling process step. The air milled additive-PTFE resin composite is then blended with a hydrocarbon extrusion aid to form a lubricated resin product, and the lubricated resin product is pressed into a preform. The preform is extruded through a selected die to produce an extruded additive-filled PTFE resin sheet or other extruded form. The extruded form is processed further as required to form the desired additive-filled PTFE resin final product.

Other objects and advantages will be apparent from the following description, claims and drawings.

DETAILED DESCRIPTION OF THE PREFERRED EMBODIMENTS

The present invention vastly expands the potential applications of additive-filled PTFE and fluorocarbon polymer based resins. With the present process a homogeneous distribution of additive within the polymer matrix can be insured. Existing methods for filling PTFE and similar polymers with additives have employed mixing methods and apparatus which do not achieve penetration of the additive within the raw material polymer matrix and, therefore, do not produce a substantially complete homogeneous distribution of the additive on, in and around the polymer. Particulate, liquid and fiber additives can be blended with a polymer matrix in accordance with the present invention to produce a macroscopically and microscopically homogeneous filled PTFE resin. Products made from such PTFE resins are free from the flaws which have plagued filled PTFE and other fluorocarbon polymer resins produced according to prior art methods.

To date the absence of a liquid phase has limited the application and blending capability of PTFE to form composite materials. PTFE must be blended with any desired additives in the solid phase. Since raw PTFE is supplied in particulate form, dispersion of a selected additive has been limited to the outer surface of the PTFE particles. The result is a discontinuous composite with varying distribution of additive on a macroscopic scale because the additive cannot penetrate the solid PTFE particles. The process of the present invention facilitates penetration of particulate, liquid, and fiber additives throughout a PTFE or other fluorocarbon polymer matrix to create an optimum distribution.

The present invention will be described with specific reference to PTFE or polytetrafluoroethylene polymers. However, it is equally applicable to other fluorocarbon polymers and similar materials.

Virgin PTFE is available as fine powders, granular powders and as aqueous dispersions. For most sheet and filament production processes, the powder forms are preferred for ease of handling and mixing. Conventionally, these raw powders are blended with desired additives and/or fillers by tumbling, rolling and the like. Care must be taken to minimize shear of the PTFE resin during blending to preserve processability and to avoid defects in the end product. Blending is usually conducted in a controlled temperature environment, preferably below 70° F., to assure minimum damage to the resin. However, the conventional blending of PTFE resins with fillers and/or additives does not achieve penetration of the polymer matrix by the filler or additive particles to produce a substantially complete homogenous dispersion of the filler or additive within the polymer matrix.

There are a number of functional considerations applicable to the fine powder PTFE blending process that influence the choice and control of the blending dynamics. Typically these include the size reduction and distribution of additive agglomerates, the manner of injection and distribution of the selected extrusion lubricant, the degree of damage imposed on the powder, the deagglomeration and agglomeration rates, the toughness of the agglomerates, the powder recirculation rate and exchange contact frequency, particle accelerations, and the complications of associated preparatory or finishing operations. Suitable balance of these functions is necessary to achieve the optimum distribution of additives within the PTFE polymer matrix. Prior to the process of the present invention, careful control and the limitation of blending time and intensity were thought to be required to avoid shear or fibrillation of the PTFE polymer. Because extrusion performance depends on an orderly and balanced fibrillation in the die zone, it is best not to shear or fibrillate the polymer prematurely. If premature fibrillation occurs during the blending step, nonuniformity through discontinuities is introduced in the polymer-additive composite. Moreover, the general reserve capacity for fibrillation in the extrusion step is reduced. This need to avoid premature fibrillation was thought to preclude the use of high energy systems for the dispersion of additives in PTFE powders. The inventors herein discovered that a high energy, high impact blending process could be employed to produce a PTFE-additive composite characterized by a complete and thorough homogeneous dispersion of the additive within the PTFE polymer matrix without damage to the polymer. The final products made from the polymer-additive composites produced according to the present method are free from the flaws and defects which would be expected from subjecting a fluorocarbon polymer to the forces generated by the blending step of this method.

Filled or additive-containing PTFE polymer products are generally produced by a multiple step method which includes blending a selected additive or filler with a PTFE powder to form a polymer-additive composite, blending a selected lubricant with the composite, and forming a preform from the lubricated composite. The preform is extruded through a suitable die to form a continuous sheet, and the sheet is calendared to the desired thickness. The lubricant is evaporated from the sheet, and the sheet is wound on a roll for storage until further processing, which typically involves stretching the extruded, calendared sheet, optionally sintering the sheet, and cutting the sheet into tapes, filaments or the like, depending on the intended end use of the additive-containing PTFE material. Exemplary end uses include laser markable materials, pigmented wire insulation, and dental floss. Contrary to the conventional wisdom of those skilled in working with PTFE polymers, the inventors have successfully blended fine powder PTFE with a wide variety of selected fillers and additives using a high energy, high impact particle to particle blending method to produce end products free from the discontinuities and other defects found in PTFE polymers subjected to shear and fibrillation-producing forces.

Figure 1:
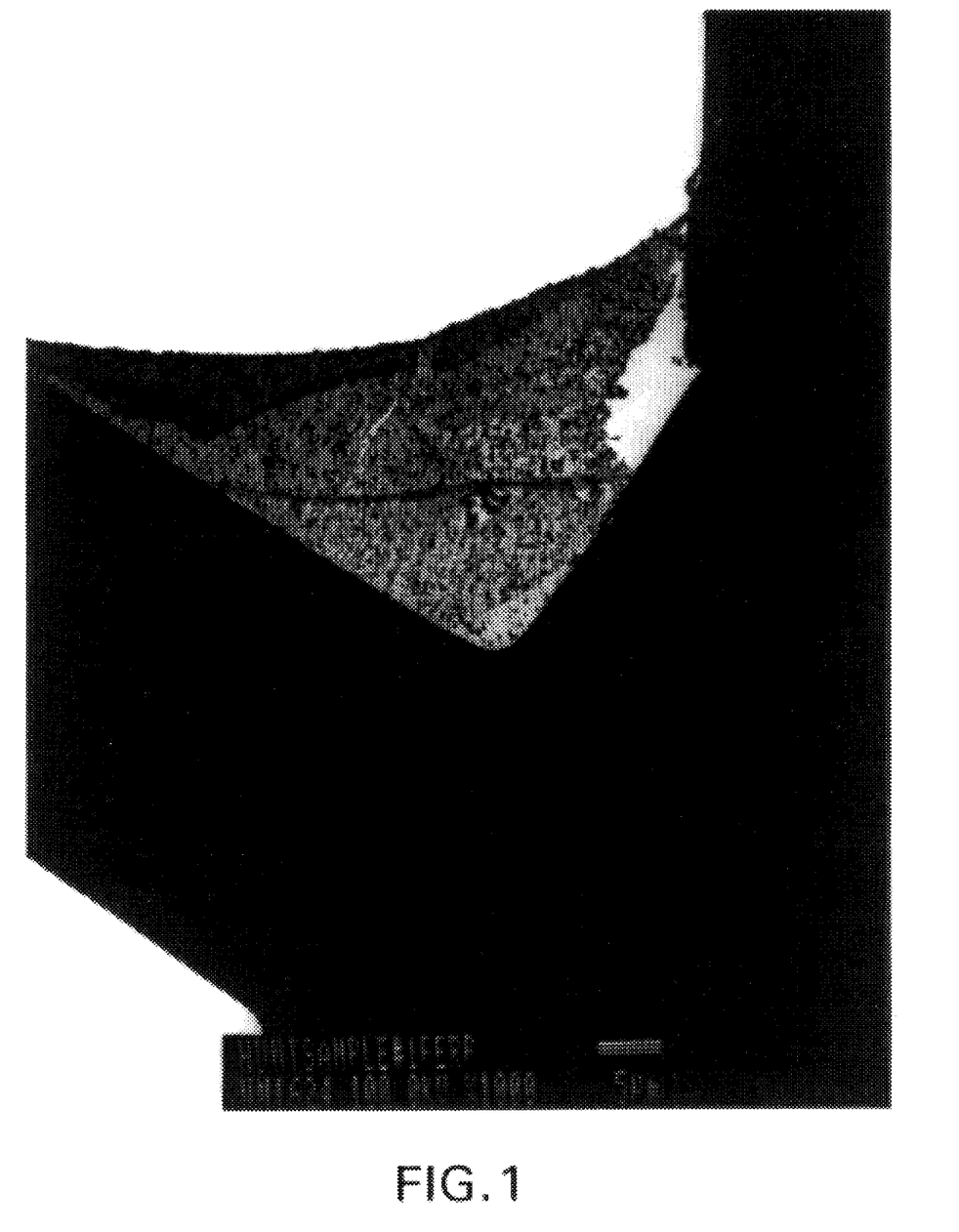
FIG. 1 is an electron micrograph showing a cross sectional view of an extruded PTFE article made of a $TiO_2$-filled PTFE polymer produced in accordance with the present invention at 1000X magnification.
Figure 2:
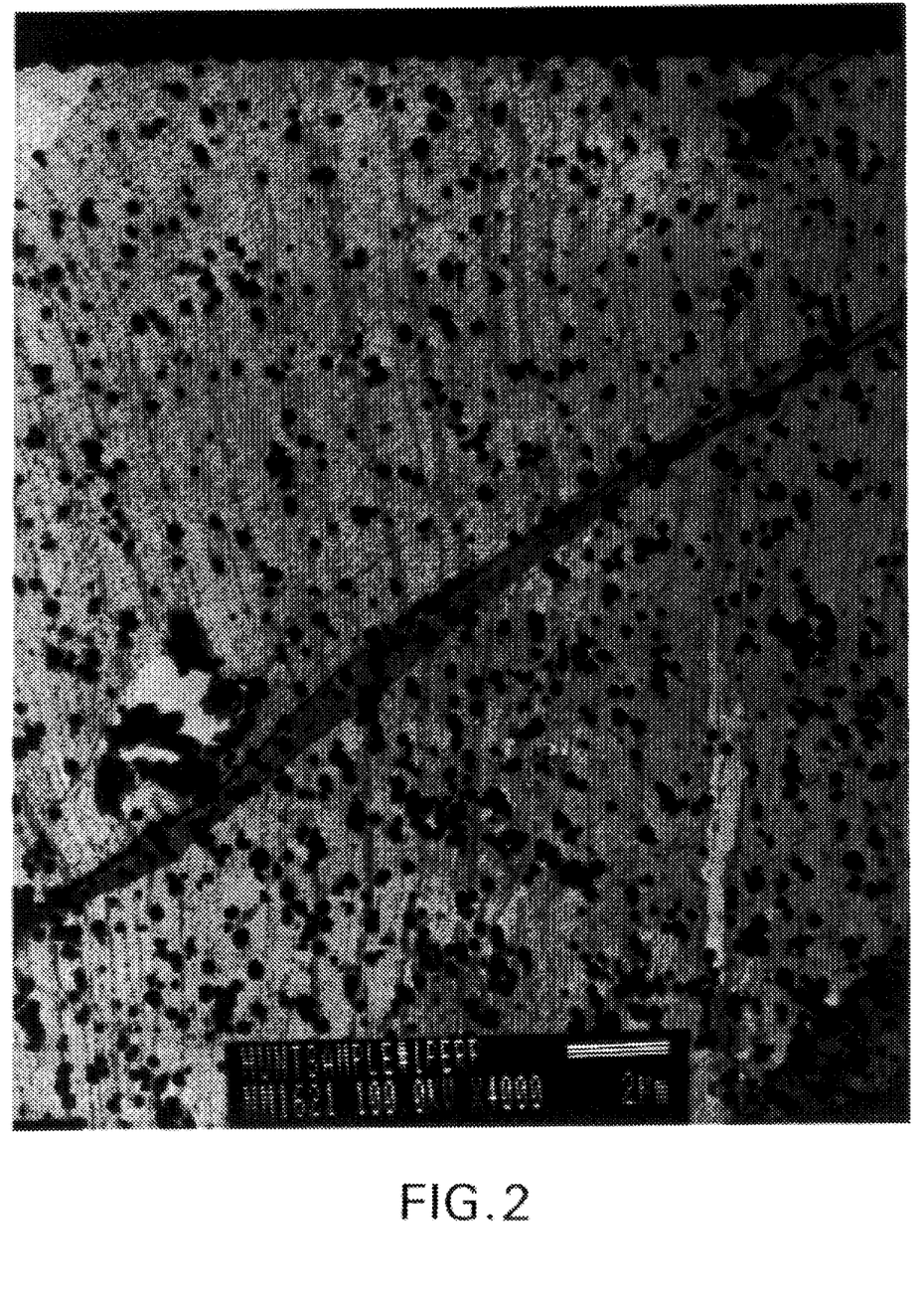
FIG. 2 is an electron micrograph of the $TiO_2$-filled PTFE of FIG. 1 at 4000X magnification.
Figure 3:
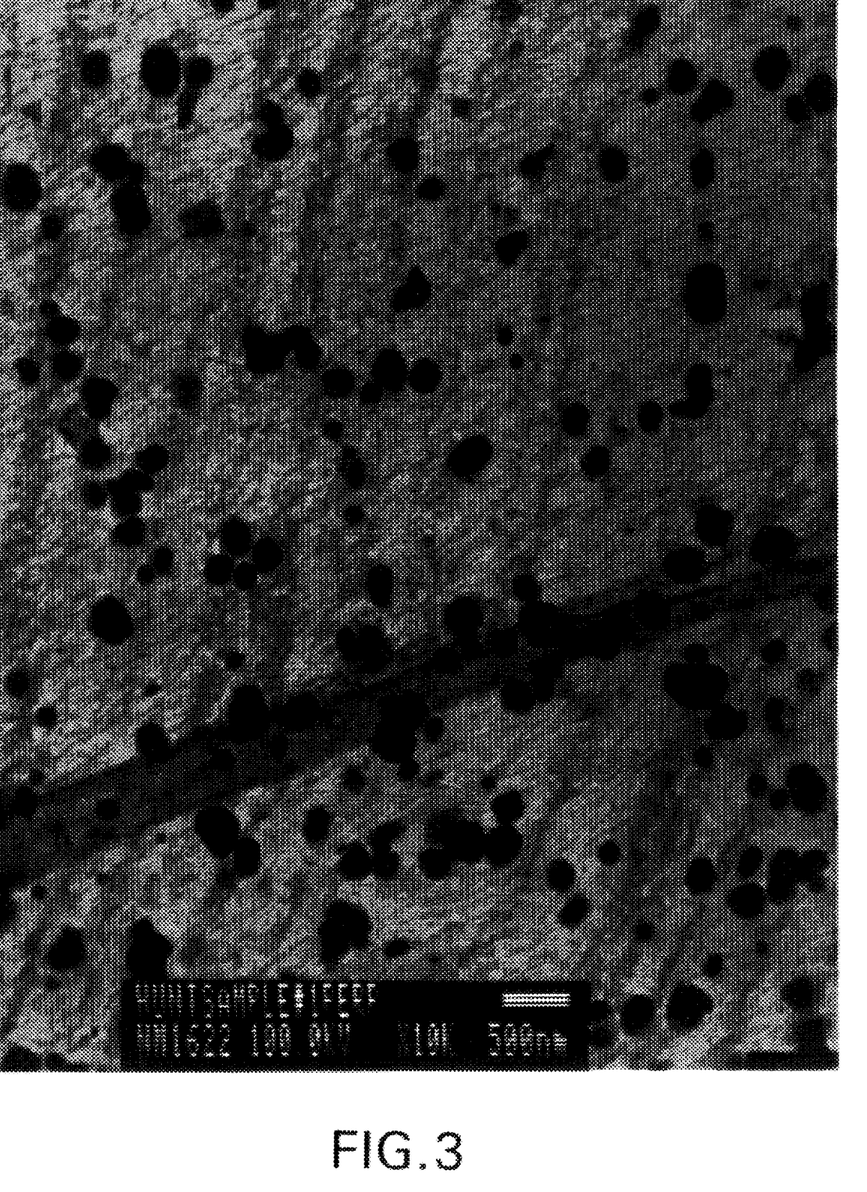
FIG. 3 is an electron micrograph of the $TiO_2$-filled PTFE of FIG. 1 at 10,000X magnification.

The present method employs an air impact pulverizer or equivalent means to impact additives into PTFE particles so that the additive particles penetrate throughout the polymer matrix. Particle to particle impact occurs between the materials to be blended and thus allows the penetration of individual additive particles into the PTFE polymer. This is in distinct contrast to existing methods, which exert little impact on individual particles and exhibit negligible penetration of additive particles into the polymer matrix. The present method permits blending with significant impact on individual particles while minimizing the contact of the PTFE with foreign bodies and forcing the necessary contact to occur between the PTFE and additive to be mixed. FIGS. 1 to 3 illustrate the degrees of dispersion possible with the blending method of the present invention.

FIGS. 1, 2 and 3 are electron micrographs of an additive-containing PTFE produced according to the process of the present invention at three different magnifications. The photosensitive material $TiO_2$ was added to fine powder PTFE and air milled as described herein. The homogeneous dispersion of the $TiO_2$ particles within the PTFE polymer matrix can be clearly seen at three different magnifications: 1000X, 4000X and 10,000X. This kind of thorough distribution of an additive within a fluorocarbon polymer matrix cannot be achieved by the blending methods conventionally employed to add fillers or additives of any kind to the polymer. Conventional blending methods distribute the additive on the outside of the polymer particles, which tends to reduce polymer-polymer bonding.

Briefly, the process of the present invention blends and then air mills a mixture of a PTFE resin and a selected filler or additive material. For most sheet and filament production processes the powder forms of PTFE are preferred for ease of handling and mixing, although a granular or molding grade PTFE could also be used. Selected additives and/or fillers are blended with the PTFE using solids blending equipment in a way that minimizes shear, for example, by tumbling or rolling under refrigerated conditions. A blender, such as the Patterson-Kelley "V" blender which tumbles powders over an inner rotating shaft is preferred for production processes because shorter blending times produce an acceptable initial dispersion. Since material shear is increased by the use of blending blades on the inner rotating shaft, use of the blades should be controlled. The polymer-additive blend is fed into a feeder, such as an FMC Vibratory Feeder, and then into an air impact pulverizer, such as the air impact pulverizers, air mills or jet mills sold under the TROST name. The resultant milled composite, or "fluff" is transferred to a blender, and a lubricant, usually a light hydrocarbon solvent, is blended with the "fluff" to facilitate the extrusion process. A preform is made from the lubricated PTFE-additive composite "fluff", and the preform is extruded and further processed to form the desired end product.

The PTFE powders preferred for use in the present invention typically have a mean particle size diameter of about 500 microns. Virtually any solid material that will withstand the processing temperatures can be used to form a solids-solids dispersion with the PTFE resin and can be used as an additive to the PTFE resin in accordance with the present process. This includes, for example, $TiO_2$ and other photosensitive materials, bioactive materials, fluoride compounds, carbon fibers, aramide fibers (such as KEVLAR), calcium carbonate, potassium carbonate, glass, graphite, lithium stearate aluminate and other lubricating agents, molybdenum disulfide, standard pigments, flavorings and a range of other organic and inorganic solids. Other illustrative additives include boron nitride, boron zeospheres, diatomaceous earth, bismuth oxide, barium sulfate, zirconium silicate, aluminum silicate, and melt processable materials such as epoxies. Fibers can be incorporated throughout the PTFE matrix only by air milling. Available polymer blending methods did not work for this purpose.

Preferably, the mean particle size diameter of the additive to be mixed with the PTFE should be about 200 microns or less or capable of being reduced to this size. In the case of fibers, a length of less than ¼ inch is desirable. The air milling step reduces particle size as the additive is incorporated into the PTFE. However, the selected additive could first be air milled to reduce its particle size if the additive material is friable or reducible. The particle size will depend on the end use of the product, however. The optimum particle size ranges from submicron to about 400–500 microns, which is the size of the PTFE polymer particles.

Additive volume or loading will also depend on the desired end product of the PTFE-additive product and the density of the additive to be incorporated into the PTFE. The optimum loading ranges are dependent on the geometry of the additive relative to the geometry of the PTFE or other polymer. Typically, the additive can constitute from about 0.05 to about 50% by weight. High loading levels cannot be achieved with low density materials. EPDM rubber, for example, can be loaded to a maximum of about 10 wt % or 30 volume %. Fibers and other high surface area materials tend to have a maximum loading of about 20 wt %. A single additive or a combination of additives can be incorporated into the PTFE. The selected additives can be in various forms, including powders, pellets and fibers. The goal is to achieve a thorough penetration of the additive or additives into the PTFE matrix while maintaining sufficient PTFE to PTFE or polymer bonding to avoid inconsistencies in the extruded product. A continuous PTFE matrix is maintained in the presence of the additives by determining optimum additive particle size and loading.

Examples of specific additives used to produce specific PTFE products or to impart selected characteristics to the PTFE include:

1. Photosensitive material such as $TiO_2$ added to PTFE to enhance high contrast laser printability after heat aging.

2. KEVLAR and/or carbon fibers added to PTFE to produce abrasion resistance and cut resistance.

3. Conductive materials such as carbon and/or metallic powders or fibers added to PTFE to enhance electrical properties.

4. Graphite and/or molybdenum disulfide added to PTFE to increase lubricity.

5. Bioactive materials such as fluorides added to PTFE to impart dental health benefits to dental floss.

The foregoing list is intended to be merely illustrative. The kind and nature of additives which can be incorporated into PTFE is limited only by processing considerations.

The process steps can be varied as required for different kinds of PTFE and to obtain maximum distribution of the selected additive in the PTFE. To illustrate, the blending cycle for the PTFE and additive in the Patterson-Kelley blender may vary from about 2 minutes to about 20 minutes, depending on whether the PTFE is a fine or molding grade, the density of the additive(s), the volume per cent, weight of the additive(s), the number of additives, the particle size of the additive(s), the surface tension of the additive(s), and the capacity of the equipment used. The feed rate of the PTFE-additive blend into the air mill by the vibrating feeder will depend on the foregoing considerations as well as the nature of the additive. For example, fibers must be fed more slowly than particulate material. A feed rate from about 1 lb. per hour to about 600 lbs. per hour can be used. The flow rate of the energy source (SCFM) will depend on the pressure of the energy input source, which could be compressed air, steam or the like. For example, 70 to 120 lbs. per hour of a mixture of PTFE and additive particles can be fed into a TROST air impact pulverizer at 70 psi of compressed air at SCFM=375 ft³/min. 70 psi is the preferred energy source pressure; however, the pressure could range from 10 to 125 psi.

The process of the present invention will be described in the production of a laser markable material and a dental floss; however, any filler and/or additive-containing PTFE product could be made according to this process. Limitation of the present invention to the production of these exemplary products is not intended.

EXAMPLE I

While a variety of laser marking methods and processes have been used in recent years, the results have not been fully satisfactory until the present. We have found that with appropriate materials, preparation and mixing, components may be produced which are simpler in structure and which may be laser marked without significant material damage or degradation and which maintain a high degree of color contrast after heat aging.

Titanium dioxide ($TiO_2$) of rutile crystal structure with purity greater than 90% is optionally air milled and classified so that the particle size ranges between 1 and 12 microns and the mean particle size is greater than 3 microns. Other photosensitive materials, for example, $SnO_2$ or ZnO, could be used instead of $TiO_2$. From 2 to 10 parts of the air milled $TiO_2$ are then mixed by tumbling in a 2 cubic foot Patterson-Kelley blender with 100 parts of a fine powder paste extrudable PTFE, such as T-60 Teflon resin available from DuPont of Wilmington, Del. One half by weight of the PTFE is added to the blender, the $TiO_2$ is loaded, and the remaining PTFE is then added. Blending is accomplished in 5 to 10 minutes. The resulting blend is then air milled to achieve a more uniform dispersion of the $TiO_2$ in the PTFE. The PTFE-$TiO_2$ blend is loaded into the feed hopper of an FMC Vibratory Feeder by scoop and is fed at 40 to 120 lb./hr. into a TROST mill generating 100 SCFM at 80 psi. 100 parts of this mixture are then blended with from 10 to 25 parts of a suitable hydrocarbon solvent, such as a light petroleum distillate, which serves as an extrusion aid. Mineral oil, kerosene, and naphtha could also be used as extrusion aids. This step may be carried out in a liquid/solids blender, such as the Twin-Shell Liquids-Solids Blender made by the Patterson-Kelley Company of East Stroudsburg, Pa. The resulting mixture is then formed at low pressure into a preform suitable for paste extrusion. The composition by weight of this preform material is about 2 to 9% $TiO_2$ about 8 to 23% extrusion aid, and the balance PTFE resin. The preform is subsequently loaded into paste extrusion equipment and either extruded directly onto a conductor, extruded into tape or ribbon which may be later slit and wrapped onto a conductor, or extruded as tubing. In either case, the composite material is then sintered. The processes and equipment for forming a preform, extruding and subsequent sintering are well known to those skilled in the art.

It has been found that conductor coverings prepared as described may be more satisfactorily marked than prior structures upon exposure to laser radiation. The standard material previously available had an initial contrast after laser marking of 48.7% and a final contrast after accelerated heat aging of 25.7%. Material made as described above has an initial contrast of 57.4% and a final contrast of 52.4% after accelerated heat aging for 234 hours at 260° C. This represents an improvement initial contrast of more than 15% and an improvement of more than 100% after heat aging as compared to the previous standard material. Only about 10% of contrast was lost by the laser markable materials produced as described upon accelerated heat aging, while prior materials lost nearly 50% of their contrast.

EXAMPLE II

The process of the present invention has been used to produce a PTFE resin-based dental floss which contains a sodium fluoride filler. Fluoride incorporated into the PTFE dental floss fibers actively leeches from the floss and is delivered to the interdental spaces during flossing. The delivery rate is directly related to the fluoride loading level. A useful loading level for fluoride in PTFE dental floss applications is 0.05 to 10% by weight. Fluoride can thus be applied to individual teeth during flossing, and the dental health benefits of fluoride can be realized during this operation as well as during cleaning of the teeth with fluoride-containing toothpaste. Dental flosses that are coated with fluoride compounds are available. However, the fluoride coating does not remain on the floss long enough to provide optimum benefit during flossing, and more complicated and expensive processing is needed to produce a coated material. The present process achieves substantially complete distribution of the fluoride in the PTFE polymer matrix by a substantially more economic method.

Sodium fluoride powder having a particle size of 30 microns is preferably air milled to an average particle size of about 5 microns. Air milling the sodium fluoride prior to blending with the PTFE avoids defects and improves the quality of the dental floss product.

A PTFE fine powder which has been stored under refrigerated conditions in a cold room (less than 70° F.) is hand scooped into a Patterson-Kelley "V" blender to which between 1 and 10% by weight sodium fluoride is then added, although the loading level of sodium fluoride will depend on the properties of the end product. Amounts of sodium fluoride outside this range may also be used effectively. The mix is dry blended for 3 minutes and then stopped. The powder adhering to the inner surfaces of the blender is scraped using a spatula, and the mix is run for a second 3 minute cycle to complete the dry blending process. This process is performed under refrigerated conditions. Once the initial blend is completed, the dry mix is then subjected to an air milling step where the PTFE-additive mix is introduced as feed to a jet mill, such as the TROST air impact pulverizer. The air milling step may be conducted at a pressure between 10 and 125 psi; however, a pressure in the range of 40 to 100 psi is preferred for the air milling of sodium fluoride and PTFE. The resultant PTFE-fluoride fluff is then recovered for the addition of lubricant.

The milled PTFE-fluoride composite is transferred to a Patterson-Kelley blender. 20 wt % D-80 lubricant (Exxon) is weighed out and added to the reservoir on the blender. The added lubricant may range from 10 to 25 wt %. The blender is then set for another three minute cycle and turned on. The lubricant is siphoned from the reservoir into the inner rotating bar where it is channeled into the mix through lube slots in the bar. The addition of lubricant is slow and continuous. The entire process takes approximately 2 minutes. The blended resin is then removed from the V blender through a butterfly valve at the bottom. The lubricated resin may be placed in a plastic lined drum, sealed, and stored under refrigerated conditions until ready to be preformed. Preforming is conducted under refrigerated conditions.

The lubricated resin is hand scooped from the drum into a 2½" preform cylinder. The dwell is set to produce a consistent preform when the barrel is filled. The preform billet is compressed to expel excess air and yield a form that is easily handled. Care is taken to prevent cracking of the preforms due to excessive pressure or short dwell times. Preforms are routinely made between 30 and 90 psi, depending on the resin, lubricant level and operator. The finished billet is 8 to 12 inches long and 2½ inches in diameter. The cylindrical billets are placed in trays lined with plastic bags which are then stacked. The finished preforms are placed in a "warm room", where they are allowed to warm to ambient temperatures of 95° F. for a minimum of 24 hours prior to extrusion. This step not only allows the preform to warm, but it allows time for the lubricant to diffuse evenly through the preforms.

Mixes of preforms are extruded as a continuous sheet and calendared to the desired thickness. The lubricant is removed from the film and wound as a jumbo roll. To accomplish this, the cylindrical preforms are placed in the extruder barrel and ram extruded through a flat die into a sheet of 0.055 inch thickness, and approximately 10 inches in width. The relatively amorphous sheet is then partially oriented using a single set of calendar rollers which reduces the film thickness from approximately 0.055 inches down to the desired thickness, which in the case of dental floss is 0.004 inches. After the calendar rollers, the 0.004 inch thick film is passed over steam heated rollers at approximately 350° F. This step vaporizes the lubricant leaving a porous membrane. The dry sheet is then taken up on a three inch mandrel as a jumbo roll. The density of the sheet at this stage is approximately 0.0577 lb/in$^3$. Typical line speeds depend on tape thickness and vary from (50 ft.min-0.002") to (30 ft/min-0.004") and beyond.

The calendared, extruded film is run through a stretch line where, after passing over a series of guide rollers, it reaches the first of a pair of ratio rollers where the stretch is initiated. Immediately thereafter, the film passes through a 52" vertical over and is heated in a unsupported state to the desired temperature, between 850° F. and 1200° F. While in the oven, the film is continuously being stretched between the ratio rollers and upon reaching the second roller the film is quenched in a water bath. At this point stretching is complete and tension only sufficient to prevent slack is applied to the film until rewound. In the floss production process a roll ratio setting of 10 and a line speed of 50 has been used as a basis, however variations in line speed, oven temperature, and stretch ratio are made to produce changes in tensile strength, density, and thickness accordingly. Additionally, the material may be subjected to multiple passes to enhance selected properties. This ratio speed combination translates into tangential ratio roller speeds of 22 ft/min and 131 ft/min respectively as measured on the control panel resulting in a 590% stretch. After the stretch, the roll is wound onto a 3 inch core in jumbo roll form again. This product may also be subjected to a second pass on the stretch line to enhance desired characteristics. The result is a semi-sintered highly directional tape with high tensile strength, in the range of 4 to 7 lb. The finished thickness of the film is between 0.0008 and 0.0012 inches.

For dental floss, the jumbo rolls are slit to 0.1" width and traverse wound on fiber cores as the finished product. The resulting product is a highly directional material with high tensile strength in the longitudinal direction.

Industrial Applicability

The process for producing PTFE or other fluorocarbon-resin-additive composites described herein will find primary application where it is desired to product an additive-containing PTFE characterized by maximum optimum distribution of the additive within the PTFE matrix to impart desired characteristics to a desired end product.

We claim:

1. A process for producing an additive-filled fluorocarbon polymer resin which microscopically and macroscopically homogeneously distributes a selected additive within the polymer matrix while maintaining sufficient polymer to polymer bonding to prevent inconsistencies in the additive-filled product, comprising the steps of:

(a) dry blending a predetermined mount of the selected additive with a selected paste extrudable fluorocarbon polymer resin for a time sufficient to intermix the additive and the polymer and to form an additive-polymer blend, wherein the selected additive has a mean particle size smaller than the mean particle size of the polymer;

(b) feeding, at a predetermined rate, the additive-polymer blend to an air impact pulverizer;

(c) milling the additive-polymer blend in said air impact pulverizer in the presence of an energy source and at a pressure selected to produce optimum particle to particle impact between said additive and said resin to substantially completely distribute the additive particles in, on and around the polymer particles while maintaining a continuous polymer matrix;

(d) blending a selected lubricant with the air milled additive-polymer blend; and (e) forming a preform suitable for extrusion from the lubricant-additive-polymer blend.

2. The process described in claim 1, wherein the fluorocarbon polymer resin is polytetrafluoroethylene.

3. The process described in claim 2, wherein said additive comprises one or more materials selected from the group consisting of photosensitive materials, bioactive materials, electrically conductive materials, pigments, flavorings, lubricants, abrasion resistance materials, and fibers.

4. The process described in claim 2, wherein said polytetrafluoroethylene is in the form of a fine powder, and said selected additive has a mean particle size smaller than the mean particle size of the polytetrafluoroethylene fine powder.

5. The process described in claim 4, wherein said polytetrafluoroethylene has a mean particle size of about 500 microns and said additive has a mean particle size in the range of less than one micron to about 450 microns.

6. The process described in claim 1, further including the step, before step (a), of air milling the selected additive to reduce the particle size of the selected additive to an optimum size that is smaller than the size of the polymer resin.

7. The process described in claim 1, further including the steps, after step (e), of extruding the preform to form an additive-filled resin sheet, processing the sheet under conditions which reduce the sheet to a desired thickness and remove the lubricant, and cutting the sheet to produce end products of a desired shape and size.

8. The process described in claim 2, wherein the additive-polytetrafluoroethylene blend of step (a) contains 0.5 to 50% by weight additive.

9. The process described in claim 2, wherein the additive-polymer blend is fed to the air impact pulverizer at a rate from about 1 lb. per hour to about 600 lb. per hour.

10. The process described in claim 2, wherein an energy input source is supplied to the air impact pulverizer during air milling of the additive-polymer blend at a pressure of from 10 to 125 psi.

11. The process described in claim 3, wherein said additive is a photosensitive material.

12. The process described in claim 3, wherein said additive is a bioactive material comprising sodium fluoride.

13. The process described in claim 7, wherein the fluorocarbon polymer resin comprises fine powder polytetrafluoroethylene, the selected additive comprises sodium fluoride, and the sheet is cut into longitudinal strips suitable for use as dental floss.

14. The product produced in accordance with the process of claim 13.

15. A process for producing an additive-filled polytetrafluoroethylene resin product characterized by the homogeneous macroscopic and microscopic distribution of a selected additive within the polytetrafluoroethylene while maintaining sufficient polytetrafluoroethylene to polytetrafluoroethylene bonding to prevent inconsistencies in the additive-filled product, comprising the steps of:

(a) selecting a predetermined amount of at least one additive from the group consisting of photosensitive materials, bioactive materials, electrically conductive materials, pigments, flavorings, lubricants, abrasion resistance materials and fibers;

(b) dry blending the selected additive with a paste extrudable, fine powder polytetrafluoroethylene polymer to form an additive-polymer blend, wherein the selected additive has a mean particle size smaller than the mean particle size of the polytetrafluoroethylene fine powder;

(c) feeding, at a predetermined optimum rate, the additive-polymer blend to an air impact pulverizer;

(d) milling the additive-polymer blend in the air impact pulverizer in the presence of an energy source at a pressure selected to produce optimum particle to particle impact between particles of the additive and particles of the polytetrafluoroethylene resin as the additive particles are distributed in, on and around the polytetrafluoroethylene particles while maintaining a continuous polytetrafluoroethylene matrix;

(e) blending a selected lubricant with the air milled additive-polymer blend;

(f) forming a preform suitable for extrusion from the lubricant-additive-polymer blend; and (g) extruding the preform and further processing the extrudate to produce the desired additive-filled polytetrafluoroethylene resin product.

16. The process described in claim 15, wherein said polytetrafluoroethylene powder has a mean particle size of about 500 microns and said selected additive has a mean particle size of from less than one micron to about 450 microns.

17. The process described in claim 15, wherein about 0.05 to 50.0% by weight of said selected additive is blended with said polytetrafluoroethylene polymer.

18. The process described in claim 15, wherein said selected additive has a mean particle size greater than about 500 microns, and said process further includes the step, before step (a), of air milling the selected additive to reduce the mean particle size of said additive to a selected optimum size less than about 500 microns.

19. The process described in claim 15, wherein the additive-polymer blend is fed to said air impact pulverizer at a rate of 70 to 120 lb. per hour.

20. The process described in claim 15, wherein the pressure in the air impact pulverizer is from 10 to 125 psi.

21. The process described in claim 15, wherein, in step (c), said energy source is compressed air at SCFM=375 ft$^3$/min, and said pressure is 70 psi.

22. A process for producing an additive-filled polytetrafluoroethylene resin product characterized by the homogeneous macroscopic and microscopic distribution of a selected additive within the polytetrafluoroethylene, including the steps of (a) selecting an amount of at least one additive selected to impart a desired characteristic to the polytetrafluoroethylene resin product, said additive having a mean particle size smaller than the mean particle size of fine powder polytetrafluoroethylene resin;

(b) dry blending 0.05 to 50.0% by weight of the selected additive with the polytetrafluoroethylene to form an additive-polytetrafluoroethylene blend;

(c) feeding the additive-polytetrafluoroethylene blend at a rate of 70 to 120 lb. per hour to an air impact pulverizer;

(d) milling the additive-polytetrafluoroethylene blend in the presence of compressed air at a pressure in the range of 10 to 125 psi in the air impact pulverizer selected to distribute the additive particles in, on and around the polytetrafluoroethylene particles and maintain a continuous polytetrafluoroethylene matrix;

(e) blending a selected lubricant with the air milled additive-polytetrafluoroethylene blend;

(f) forming a preform suitable for extrusion from the lubricant-additive-polytetrafluoroethylene blend;

(g) extruding the preform to form a sheet; and (h) further processing the sheet as required to form the desired additive-filled polytetrafluoroethylene resin product.

23. The process described in claim 22, wherein said at least one additive is selected from the group consisting of photosensitive materials, bioactive materials, electrically conductive materials, pigments, lubricants, flavorings, abrasion resistance materials and fibers.

24. The process described in claim 23, wherein said sheet is sintered.

25. The process described in claim 24, wherein said at least one additive is a bioactive material comprising sodium fluoride and the desired product is dental floss.

26. The process described in claim 22, further including the step, before step (a), of air milling the selected additive to reduce the mean particle size of the selected additive to an optimum size that is smaller than the mean particle size of the polytetrafluoroethylene resin particles.

27. The process described in claim 15, wherein step (g) comprises extruding the preform to form an additive-filled resin sheet, processing the sheet under conditions which reduce the sheet to a desired thickness and remove the lubricant, and cutting the sheet to produce end products of a desired shape and size.

28. The process described in claim 15, wherein said additive is a photosensitive material.

29. The process described in claim 15, wherein said additive comprises fibers.

30. The process described in claim 15, wherein said additive-containing polytetrafluoroethylene polymer is sintered after said preform is extruded.

31. The process described in claim 17, wherein 20% by weight of fibers having a length less than ¼ inch is blended with said polytetrafluoroethylene polymer.

32. The process described in claim 31, wherein said fibers are aramide or carbon fibers.

33. The process described in claim 15, wherein said at least one additive is selected from the group consisting of titanium dioxide, fluoride compounds, calcium carbonate, potassium carbonate, glass, graphite, lithium stearate aluminate, molybdenum disulfide, boron nitride, boron zeosheres, diatomaceous earth, bismuth oxide, barium sulfate, zirconium silicate, aluminum silicate and epoxy compounds.

* * * * *